(12) United States Patent
Licitra et al.

(10) Patent No.: US 8,248,621 B2
(45) Date of Patent: Aug. 21, 2012

(54) METHOD FOR OPTICAL CHARACTERISATION

(75) Inventors: Christophe Licitra, Grenoble (FR);
Maxime Besacier, Saint Jean de Moirans (FR); Régis Bouyssou, Fontaine (FR); Thierry Chevolleau, Grenoble (FR); Mohamed El Kodadi, Grenoble (FR)

(73) Assignees: Commissariat à l'énergie atomique et aux énergies alternatives, Paris (FR);
Centre national de la recherche scientifique (C.N.R.S.), Paris (FR)

( * ) Notice: Subject to any disclaimer, the term of this patent is extended or adjusted under 35 U.S.C. 154(b) by 168 days.

(21) Appl. No.: 12/836,548

(22) Filed: Jul. 14, 2010

(65) Prior Publication Data

US 2011/0019207 A1    Jan. 27, 2011

(30) Foreign Application Priority Data

Jul. 20, 2009    (FR) ...................................... 09 55027

(51) Int. Cl.
*G01B 11/14* (2006.01)
(52) U.S. Cl. ...................................................... 356/625
(58) Field of Classification Search .................. None
See application file for complete search history.

(56) References Cited

U.S. PATENT DOCUMENTS 7,196,782 B2 * 3/2007 Fielden et al. .................. 356/72
7,751,046 B2 * 7/2010 Levy et al. .................... 356/401

FOREIGN PATENT DOCUMENTS

WO    WO 00/12999    3/2000

OTHER PUBLICATIONS

"Développement de la scatterométrie dynamique pour le suivi en temps réel de procédés. Application à la microélectronique"; "Development of dynamic scatterometry for real time process control. Applications for microelectronics"; Soulan, Sebastien; PHD Thesis, Université Grenoble 1—Joseph Fourier; Version 1, Nov. 19, 2008; pp. 1-156.

* cited by examiner

*Primary Examiner* — Tu Nguyen
(74) *Attorney, Agent, or Firm* — Pillsbury Winthrop Shaw Pittman, LLP

(57) ABSTRACT

An optical characterization method of repeat units forming a diffraction structure, each repeat unit including a geometric pattern produced, at least in part, using a porous material, the method including: determining the geometric parameters of the patterns; performing a scatterometric acquisition using an optical measurement system of the experimental optical response of the diffraction structure placed in a chamber at a given pressure, a presence of an adsorbable gaseous substance in the chamber causing condensation of the adsorbable gaseous substance in a part of open pores of the patterns; and determining a theoretical optical response of the diffraction structure from the determined geometric parameters and by adjusting an optical index of the material of an area of each of the patterns, in which the adsorbable gaseous substance has condensed, to make a difference between the experimental response and the theoretical response less than or equal to a given threshold.

22 Claims, 7 Drawing Sheets

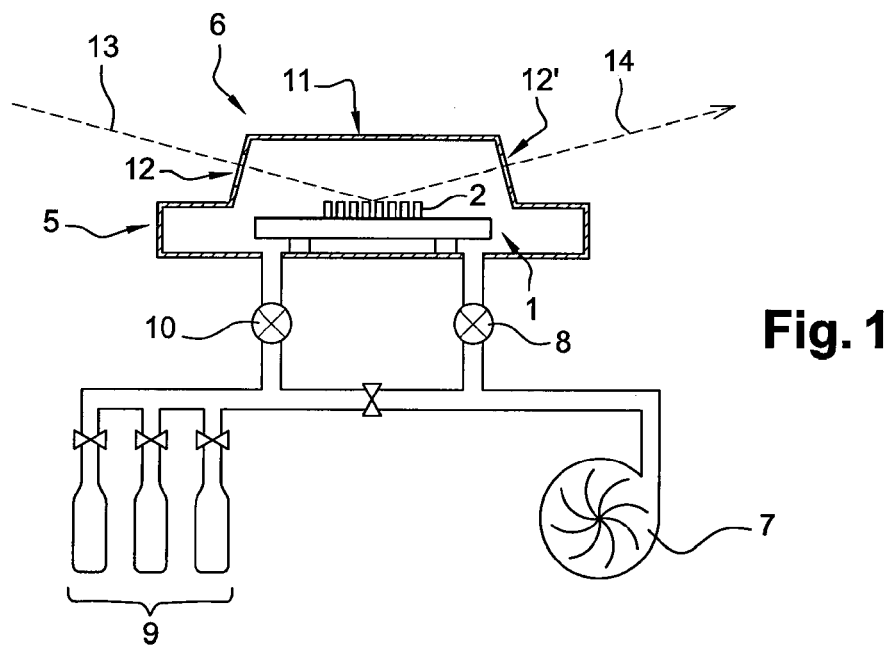
Fig. 1
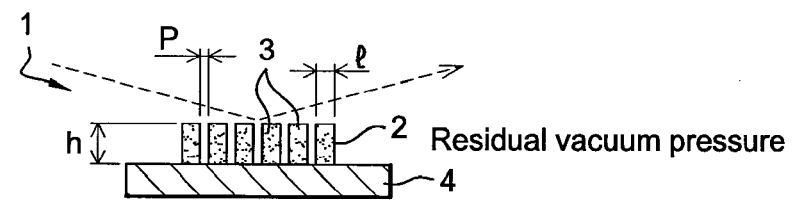
Fig. 2a Residual vacuum pressure
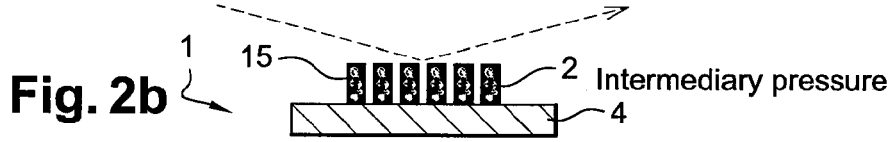
Fig. 2b Intermediary pressure
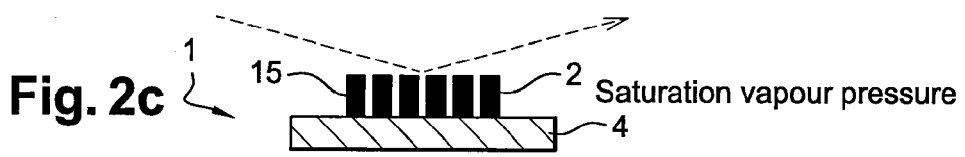
Fig. 2c Saturation vapour pressure
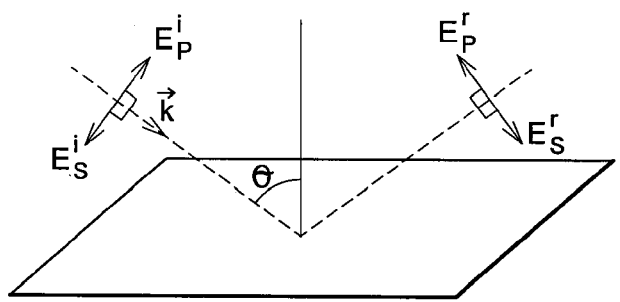
Fig. 3

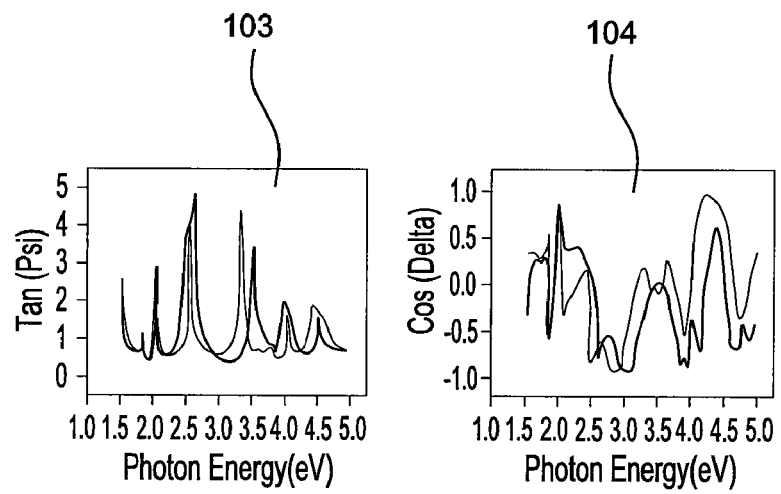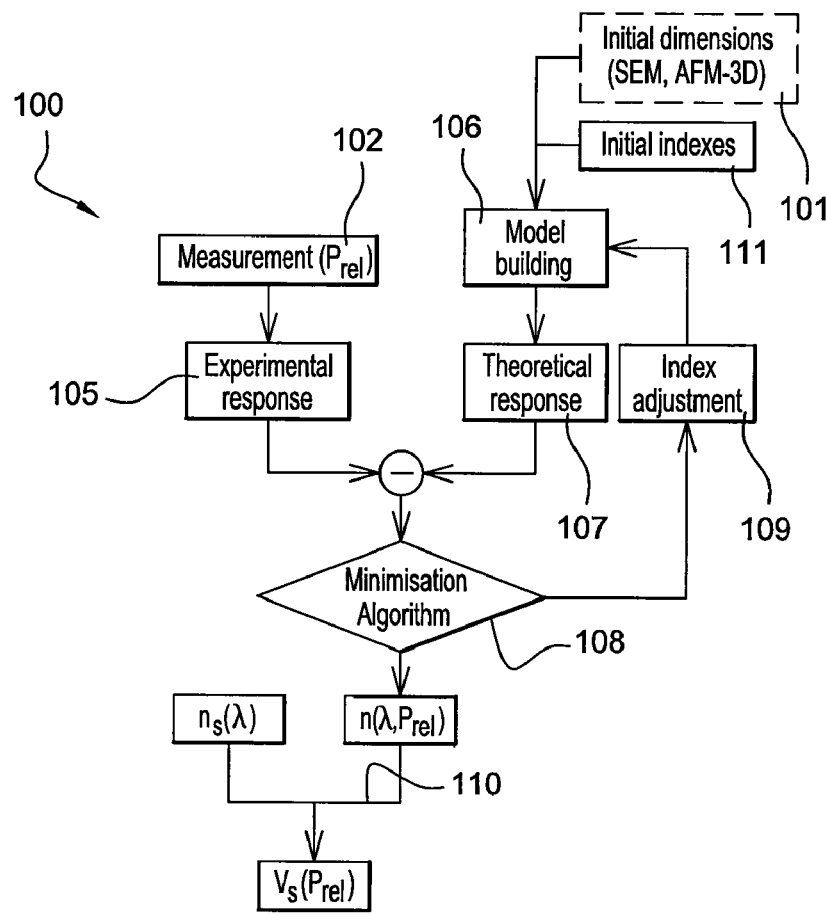
Fig. 4

METHOD FOR OPTICAL CHARACTERISATION

CROSS-REFERENCE TO RELATED APPLICATIONS

This application is based upon and claims the benefit of priority from French patent application Ser. No. 09/55027, filed Jul. 20, 2009, the entire content of which is incorporated herein by reference.

BACKGROUND

1. Field

This invention relates to a method for optical characterisation. The method according to the invention is more particularly suited to the characterisation of porous materials used in microelectronic integrated circuits.

2. Description of Related Art

The interconnect structures for microelectronic integrated circuits, for example transistors, are normally produced from metallic lines, typically made out of Aluminium or Copper. These metallic lines are separated by a dielectric material which serves as insulation as much in a lateral manner for the lines as in a vertical manner for the levels of metal. The problem involves overcoming deterioration in the electrical characteristics of the dielectric materials located between the metallic interconnect lines when the size of said lines is reduced. Indeed, improving transistor properties is connected to the reduction in their sizes, which leads to a reduction in the sizes of the lines and spacing between these lines. Unfortunately, moving these lines closer together causes interline parasitic capacitances to appear.

In a known manner, one means for maintaining performance levels involves replacing the dielectric material of the interlines with a low dielectric constant material, enabling the capacitive coupling between the adjacent lines to be reduced. One solution for lowering the dielectric constant consists in introducing porosity into the dielectric material. A major difficulty however resides in the notion of conserving the porous properties of the material during its integration into microelectronic circuits.

Therefore, the porous properties of these low dielectric constant materials must be capable of being controlled.

A first known solution enabling the porosity and size of the pores to be characterised consists in using an adsorption technique coupled with a mass measurement. These weight measurements nevertheless require dense samples in order to observe a significant variation in mass during the adsorption process.

Another known solution enabling the porosity and size of pores to be characterised for materials placed in a thin layer consists in using an adsorption technique coupled this time with an ellipsometric measurement. Such a process is described in particular in the patent application WO 00/12999. Nevertheless, such a solution presents some disadvantages.

Indeed, when integrating the porous materials into microelectronic circuits, a problem arises involving the capacity to measure the properties of said materials during the integration process, i.e. when they are no longer in the form of thin films, but in the form of patterns originating from standard lithography and etching processes, as the measurements taken by porosimetric ellipsometry are suitable for measuring thin porous films. Such a solution therefore does not enable the porous material to be characterised close to its final use, i.e. when it is in the form of porous patterns originating from lithography and etching processes. This pattern characterisation is fundamental insofar as the properties of the porous materials can evolve during the lithography and etching processes.

SUMMARY

In this context, the purpose of this invention is to provide a method for non-destructive optical characterisation, in particular enabling the properties of porous materials to be obtained when the latter are integrated into microelectronic circuits.

For this purpose, the invention relates to a method for the optical characterisation of repeat units repeated in a regular manner so as to form a diffraction structure, each repeat unit comprising at least one geometric pattern, each of said patterns being produced, at least in part, using a porous material, said method comprising the steps for:

determining the geometric parameters of said patterns;

the scatterometric acquisition of the experimental optical response of said diffraction structure placed in a chamber at a given pressure, the presence of an adsorbable gaseous substance in said chamber causing the condensation of said substance in at least one part of the open pores of the patterns of the structure;

determining the theoretical optical response of said diffraction structure from the geometric parameters determined and by adjusting the optical index of the material of the area of each of said patterns, in which the adsorbable gaseous substance has condensed, so as to make the difference between said experimental response and said theoretical response less than or equal to a given threshold.

The term porous material refers to a material capable of adsorbing the adsorbable gaseous substance used when the latter is maintained under pressure and in contact with the material.

The term optical index of the porous material refers to the complex effective index of this porous material with the condensed adsorbable gaseous substance, the real part of this index corresponding to the refractive index and the imaginary part corresponding to the extinction coefficient. The refractive index of the material with the condensed adsorbable gaseous substance demonstrates the fact that the different wavelengths do not cross the material at the same speed and induces a change in direction of a light ray when crossing a dioptre according to the Descartes law.

The term optical response refers to any type of optical response of the diffraction structure that is to be characterised, whether the measurement technique involves ellipsometry (spectometric or goniometric) or reflectometry (spectroscopic or goniometric).

The adsorbable gaseous substance is preferably selected so that the interaction between the condensed adsorbable gaseous substance and the porous material is as small as possible. Moreover, the adsorbable gaseous substance is preferably introduced into the pressurised chamber at a room temperature of 21° C. and has a condensation temperature of between 25° C. and 100° C. and an equilibrium pressure of between 10 and 100 Torr. In the previous example, the measurements can be taken at room temperature. Some organic solvents in vapour form can be used as an adsorbable gaseous substance.

The term open pores refers to the pores connected to the surface of the material (i.e. those in which the adsorbable gaseous substance is capable of condensing from the surface of the material).

With this invention, scatterometry is used advantageously over the spectral range enabling a diffraction pattern to be obtained (typically for a dielectric material such as porous SiOCH, the useable spectral range including the UV and visible range). Scatterometry will enable the index of the porous material to be determined at a given pressure and for each wavelength of the spectral range used. The technique of scatterometric characterisation consists in taking a measurement on the diffraction structure using a polarised electromagnetic wave. The evolution of the index of the porous material can thus be monitored according to the pressure in the chamber by taking several measurements at different pressures within the chamber. In a known manner, in classic scatterometry processes, only the dimensions of the patterns are determined (typically the width, height and possibly the slope of the sidewalls) and the material indexes are fixed during the analysis. On the other hand, when taking a porosimetric scatterometry measurement according to the invention, the effective index of the material (porous material+ condensed adsorbable gaseous substance) changes according to the quantity of substance adsorbed in the pores, and it is this index that will be adjusted according to the experimental conditions in such a way as to characterise the porosity of the material. In other words, the scatterometric analysis is adapted to the problematic of porosimetry, not by adjusting the dimensions of the patterns, but by adjusting the index of the porous part of the pattern at each measurement. Modelling of the indexes at each step of the adsorption phase and the desorption phase is thus required. Unlike with classic scatterometry, where the dimensions are determined, the method according to the invention integrates the prior step of determining (at least in part) the dimensions of the patterns, these dimensions then being frozen during the optical index adjustment steps with measurements under pressure. The dimensions can, for example, be determined with a first measurement in a vacuum or with the use of additional characterisations such as measurements taken by scanning electron microscopy (SEM) or by atomic force microscopy in three dimensions (AFM-3D). Modelling of the patterns to obtain a theoretical signature can, for example be obtained by a rigorous coupled-wave analysis method (RCWA). Finally, the index of the porous material at a given wavelength can then be used to determine the quantity of adsorbable gaseous substance that has condensed in the pores of the material according to the pressure of the adsorbable gaseous substance within the chamber using a law of effective medium approximation (EMA).

Unlike with porosimetric ellipsometry, which is performed on a thin film, the method according to the invention relates to a method for non-destructive measurement by optical means capable of determining the properties of porous patterns close to their use within the microelectronic circuit; these properties can be, for example: the porosity, size distribution of the pores, diffusion kinetics, permeability and wettability of the porous material.

The method according to the invention can also include one or several of the features described hereinafter, considered either on an individual basis or according to any combination technically possible:
- the size of said diffraction structure is larger than the size of the optical spot used for the scatterometric measurement;
- said diffraction structure comprises at least ten patterns;
- each pattern is a line made out of dielectric material capable of insulating two metallic lines;
- the scatterometric acquisition is performed by ellipsometry;
- the step for determining the geometric parameters of said patterns comprises a step for the scatterometric acquisition of the experimental optical response of said diffraction structure placed in the chamber in a vacuum and a step for determining the theoretic optical response of said diffraction structure from the optical indexes of the patterns in a vacuum and by adjusting the dimensions of said patterns so as to make the difference between said experimental response and said theoretical response less than or equal to a given threshold;
- advantageously, the step for determining the geometric parameters of said patterns comprises a step for measuring by scanning electron microscopy and/or by atomic force microscopy in three dimensions; this step enables a real image of the pattern to be obtained, which complements the geometric parameters obtained by scatterometry in a vacuum (which uses the theoretical shapes and dimensions of the patterns as input parameters). It is possible that the real image of the pattern differs from the pattern sought to be produced (typically, problems connected to the etching process can cause the shape of the sidewalls to be different from that expected). In this event, the use of SEM or AFM-3D measurements seems particularly useful.
- the method according to the invention comprises a plurality of steps for scatterometric acquisition at different given pressures, each acquisition step being followed by a step for determining the theoretical optical response of the diffraction structure by adjusting the optical index;
- the method according to the invention comprises a step for determining said optical index, adjusted according to pressure over the entire range of wavelengths used for the scatterometric acquisition steps;
- said plurality of steps for scatterometric acquisition at different given pressures is performed according to an increasing variation in pressure corresponding to the progressive adsorption of said adsorbable gaseous substance in the open pores of said patterns and/or according to a decreasing variation in pressure corresponding to the progressive desorption of said adsorbable gaseous substance in the open pores of said patterns;
- the pressure varies from a residual vacuum pressure to the saturation vapour pressure of said adsorbable gaseous substance and/or from the saturation vapour pressure of said adsorbable gaseous substance to a residual vacuum pressure;
- the optical index of the adjusted material at a given pressure is used to determine the quantity of adsorbable gaseous substance that has condensed in the open pores;
- determining the quantity of adsorbable gaseous substance condensed is performed by determining the volume fraction of the adsorbable gaseous substance condensed in the open pores via a law of effective medium approximation (EMA);
- the method according to the invention comprises a step for determining the size distribution of the open pores;
- the value of the rate of apparent porosity of said porous material forming, at least in part, said patterns, is obtained by adjusting the optical index to the saturation vapour pressure of said adsorbable gaseous substance;
- each of said patterns comprises a first upper layer made out of a non-porous material positioned on the surface of a second layer comprising at least one part made out of a material not capable of adsorbing the adsorbable gaseous substance used when the latter is maintained under pressure in contact with the material, and at least one part, such as one of its sidewalls, made out of a porous material, the difference between the experimental response at a given pressure and the theoretical response being made less than or equal to a given limit by adjusting:

the optical index of the material of the area of said porous part in which the adsorbable gaseous substance has condensed and;

a geometric parameter representing the size of the area of said porous part in which the adsorbable gaseous substance has condensed;

said method comprising a plurality of steps for scatterometric acquisition at different given pressures, each acquisition step being followed by a step for determining the theoretical optical response of the diffraction structure by adjusting said optical index and said geometric parameter;

said adsorbable gaseous substance is a polar solvent such as water;

each of said patterns comprises a first upper layer made out of a non-porous material positioned on the surface of a second layer made out of a porous material, the difference between the experimental response at a given pressure and the theoretical response being made less than or equal to a given threshold by adjusting:

the optical index of the material of the area of said second layer in which the adsorbable gaseous substance has condensed and;

a geometric parameter representing the size of the area of said second porous layer in which the adsorbable gaseous substance has condensed;

said method comprising a plurality of steps for scatterometric acquisition according to the time of diffusion of said adsorbable gaseous substance within said second layer from the sidewalls of the latter, each acquisition step being followed by a step for determining the theoretical optical response of the diffraction structure by adjusting said optical index and said geometric parameter;

the material of the non-porous layer in addition to its thickness are chosen so that said non-porous layer is transparent to the wavelengths used for the scatterometric acquisition steps;

an upper layer made out of a permeable material to be characterised is positioned on the upper surface of the patterns made out of a porous material, the difference between the experimental response at a given pressure and the theoretical response being made less than or equal to a given threshold by adjusting:

the optical index of the material of the area of said porous patterns in which the adsorbable gaseous substance has condensed and;

a geometric parameter representing the size of the area of said porous patterns in which the adsorbable gaseous substance has condensed;

said method comprising a plurality of steps for scatterometric acquisition according to the time of diffusion of said adsorbable gaseous substance within said patterns from the sidewalls of the latter, each acquisition step being followed by a step for determining the theoretical optical response of the diffraction structure by adjusting said optical index and said geometric parameter;

said step for determining the theoretical optical response of said diffraction structure is performed by a rigorous coupled-wave analysis method (RCWA).

BRIEF DESCRIPTION OF THE DRAWINGS

Other characteristics and advantages of the invention can be clearly observed in the following description, which is given for indicative and in no way limiting purposes, with reference to the attached figures, among which:

FIG. 1 illustrates in a schematic manner the principle and operating conditions of an optical measurement which can be used in the method according to the invention;

FIGS. 2a to 2c are enlargements of the structure to be characterised represented in FIG. 1, corresponding to different states of adsorption of the adsorbable gaseous substance in the patterns;

FIG. 3 illustrates the principle of spectroscopic ellipsometry;

FIG. 4 illustrates a first embodiment of the method according to the invention;

DETAILED DESCRIPTION

Figure 5:
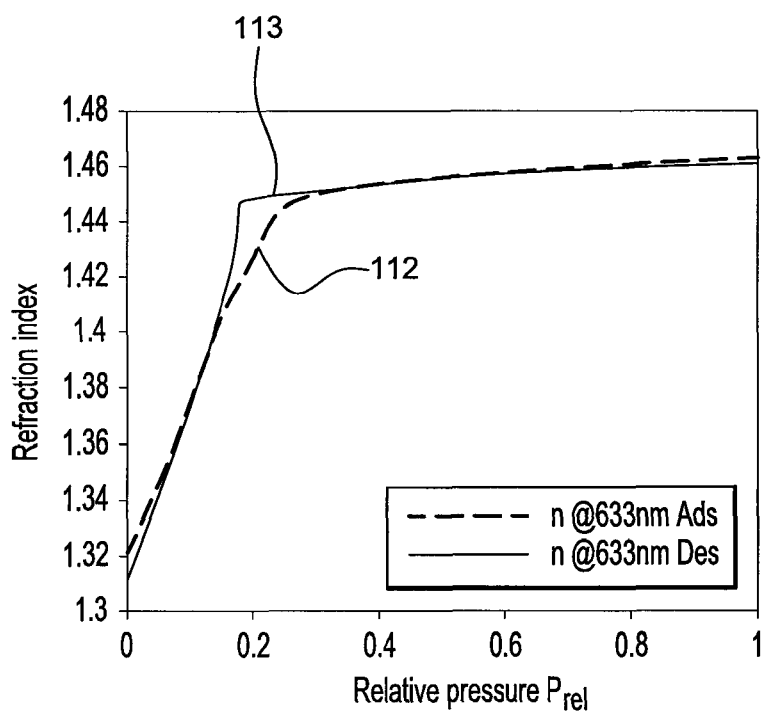
FIG. 5 represents an example of evolution, during adsorption and desorption, of an effective refractive index determined by the method according to the invention according to the relative pressure at a given wavelength.

FIG. 1 illustrates in a schematic manner the principle and operating conditions of an optical measurement which can be used in the method according to the invention. A structure 1 can be, seen, that must be characterised optically, forming a diffraction grating. FIG. 2a is an enlargement of the diffraction structure 1 represented in FIG. 1. Structure 1 comprises a plurality of identical or substantially identical patterns 2 positioned periodically (i.e. regularly spaced according to a spacing period P). These patterns 2 are porous patterns, i.e. made, at least in part, from a porous material such as a dielectric material, in which porosity has been introduced. The term porous pattern refers to a pattern integrating a plurality of holes 3 (the points representing the material) with variable sizes within the material and enabling an adsorbable gaseous substance to be adsorbed. These patterns 2 are preferably parallel porous lines spaced apart by a distance P and whose porosity is to be characterised. Each pattern 2 (substantially having a height h and a width l) is formed on a substrate 4, diffraction structure 1 having at least ten parallel porous lines 2. The characteristic size of the patterns 2 of structure 1 (i.e. the width l of line 2) is preferably equal to the size of the dielectric strips insulating two metal lines (typically the width of the metal lines when the lines 2 are made out of a porous dielectric material for insulating said metallic lines). Such a diffraction structure 1 can normally be used in service areas of microelectronic masks (area referred to as scatterometric, usually for measuring the dimensions of the patterns); in other words, this example involves a dedicated area (service area) on the wafer, which will then be lost during the cutting operation; another method can consist in creating test samples representing the actual configuration of the dielectric lines. The overall size of diffraction structure 1 is bigger than the size of the optical spot used (typically 50 µm to 200 µm in diameter) so that the area of measurement is contained within structure 1.

All or part of the porosity of the porous material used for pattern 2 is classed as open, i.e. connected to the surface of the material; it is this open area (open porosity) that will then be characterised. Structure 1 is placed in a chamber 5 of a porosimetric ellipsometry device 6.

Porosimetric ellipsometry device 6 comprises:
chamber 5;
a pump 7 to modify the pressure within chamber 5, said pump being connected to chamber 5 via a control valve 8;
means 9 (typically reservoirs 9 containing the adsorbable gaseous substance) to supply chamber 5 with the adsorbable gaseous substance, means 9 being connected to chamber 5 via a control valve 10;
a pressure gauge 11 to measure the pressure within chamber 5;
a window 12 through which the light signal may pass so as to perform the measurement and a window 12' through which the light signal may leave.

Structure 1 is lit by a specular light wave 13 at a given wavelength, emitted by a light source that is not represented; the reflected light 14 forms the experimental optical response of structure 1 being analysed. It is understood that measurements can be made using different wavelengths for the incident wave.

With the configuration of device 6, an adsorbable gaseous substance can be injected into chamber 5 via supply means 9 and control valve 10, and the pressure can be varied within chamber 5 by pump 7 and control valve 8.

For purely illustrative purposes, the adsorbable gaseous substance can be obtained from toluene, methanol, water or isopropanol.

A sequence for the adsorption and desorption of the adsorbable gaseous substance can thus be performed on structure 1 whereas the scatterometric optical acquisition is performed in parallel on the same structure according to the pressure of the adsorbable gaseous substance within chamber 5.

In this manner, the scatterometric acquisition of the experimental optical response of diffraction structure 1 can be performed repeatedly with the pressure in chamber 5 varying:

for adsorption, the pressure varies from a residual vacuum (the term residual vacuum typically refers to a pressure within chamber 5 of between $10^{-2}$ and $10^{-3}$ Torrs) to the saturation vapour pressure of the adsorbable gaseous substance used for the experiment (typically between 10 and 100 Torrs according to the adsorbable gaseous substances and the room temperature), for desorption: the pressure varies inversely, from the saturation vapour pressure of the adsorbable gaseous substance to the residual vacuum.

During the adsorption step (or in a symmetrical manner for desorption), the state of porous structure 1 will evolve in the following manner: at a residual vacuum pressure, the pores are empty (FIG. 2a), then, as the pressure in chamber 5 increases (intermediary pressure between the residual vacuum pressure and the saturation vapour pressure of the adsorbable gaseous substance), a threshold is reached, at which the adsorbable gaseous substance condenses in the smaller pores (FIG. 2b illustrates this phenomenon, where the adsorbable gaseous substance 15 can be observed beginning to fill the pores of the patterns 2). Finally, as the pressure increases further to reach the saturation vapour pressure of the adsorbable gaseous substance, the larger pores are also filled by capillary condensation (FIG. 2c illustrates this phenomenon). Above the saturation vapour pressure, the increase in pressure no longer affects the filling of the pores and the experiment ends when the saturation vapour pressure has been reached.

In a continuous manner, the base principal of ellipsometry is to measure the changes in the polarisation state of the light induced by reflection from a surface being analysed. FIG. 3 illustrates this principle in a general manner, with the wave vector k representing the direction of incidence of the wave forming an angle θ with the normal to the plane of the surface being analysed. The incident electric field $E^i$ can be broken down into a component $E_p^i$ parallel to and a component $E_s^i$ perpendicular to the plane of incidence. In a similar manner, the reflected electric field $E^r$ can be broken down into a component $E_p^r$ parallel to and a component $E_s^r$ perpendicular to the plane of incidence.

The ellipsometry measurement therefore consists in measuring the magnitude:

$$\rho = \tan(\psi)e^{j\Delta} = \frac{r_p}{r_s}, \quad (1)$$

where $r_p$ and $r_s$ are the ratios (for components p and s respectively) of the magnitudes of the incident and reflected fields:

$$r_p = \frac{E_p^r}{E_p^i} \text{ and } r_s = \frac{E_s^r}{E_s^i}.$$

The value of ρ is not only dependent on the sample targeted by the light ray but also on the wavelength λ.

With spectroscopic ellipsometry, characterisation of the object is performed by varying the wavelength λ over a known range.

Scatterometry consists, for example, in performing an ellipsometric measurement on a periodic sample by advantageously using light diffraction: a priori, if information is available indicating that the sample is periodic, more information can therefore be collected than with simple ellipsometry.

In a general manner, an ellipsometric measurement system provides a pair of signals for each wavelength. Several pairs are often used; in the following text, the pair (ψ, Δ), will be mentioned, where ψ and Δ are the magnitudes defined above with reference to formula (1). In this particular case, according to the embodiment described herein, the spectroscopic ellipsometry device provides two signatures tan(ψ) and cos (Δ) according to the wavelength λ.

FIG. 4 illustrates the different steps involved in a first embodiment of a method 100 according to the invention.

The first step 101 of method 100 according to the invention consists in determining at least one part of the dimensions (typically dimensions h and l, or even the slope of the sidewalls) of patterns 2 of structure 1 as represented in FIG. 1. This determination can, for example, be obtained by a measurement taken by scanning electron microscopy (SEM) or by atomic force microscopy in three dimensions (AFM-3D). A first scatterometric acquisition can also be made for the experimental optical response of diffraction structure 1 placed in chamber 5 in a residual vacuum (state of structure 1 represented in FIG. 2a). This first acquisition constitutes a standard use of scatterometry; in other words, from a structure made out of a known material with a known initial optical index without any gaseous substance adsorbed in the patterns (step 111), the geometric magnitudes h and l of the profile of structure 1, previously modelled, are determined.

A sequence for the adsorption and desorption of the adsorbable gaseous substance is performed on structure 1 whereas scatterometric optical acquisition 102 is performed in parallel on the porous grating for each pressure of the adsorbable gaseous substance within chamber 5. In other words, for a relative pressure $P_{rel}$ of adsorbable gaseous substance in chamber 5, two signatures are obtained: $\tan(\psi)$ and $\cos(\Delta)$ according to the wavelength $\lambda$ (a plurality of $\tan(\psi)$ and $\cos(\Delta)$ signatures corresponding to the different measurement pressures are represented in frames 103 and 104 according to the energy E transported by the photons expressed in eV, the energy E being directly dependent on the wavelength $\lambda$ by the formula $E=h \cdot c/\lambda$ where h represents the Planck constant and c the speed of light). An experimental optical response 105 is thus obtained according to the wavelength for each pressure. The relative pressure $P_{rel}$ of the adsorbable gaseous substance in chamber 5 is given by the formula: $P=P/P_s$ where P is the pressure in chamber 5 and $P_s$ is the saturation vapour pressure of the adsorbable gaseous substance.

In a general manner, the optical signature of a grating is known to change according to its dimensions or the optical index of the materials from which it is comprised. In classic scatterometry processes, only the dimensions of the lines are determined (width, height, slope of the sidewalls) and the material indexes are fixed during the analysis.

However, according to the invention, the dimensions are fixed and calculated during the first step 101 using additional characterisations such as the SEM or AFM-3D or using a first measurement in a vacuum. For each measurement 102 using porosimetric scatterometry, the effective material index (i.e. the index of the unit including the porous material forming pattern 2 and the adsorbable gaseous substance condensed in the open pores of patterns 2) changes according to the quantity of gaseous substance condensed in the pores.

The method according to the invention also comprises, for each relative pressure $P_{rel}$, a step 107 for determining the theoretical optical response of structure 1 using a simulation method 106. Modelling of the patterns to obtain a theoretical signature can, for example, be obtained by a rigorous coupled-wave analysis method (RCWA) or modal method by Fourier expansion (MMFE). Such a method of modal decomposition is particularly described in the thesis "Développement de la scattérométrie dynamique pour le suivi en temps réel de procédés. Application à la microélectronique" (Development of dynamic scatterometry for real time monitoring of processes. Application in microelectronics" (Sébastien Soulan—University of Grenoble I—Joseph Fourier-Viva voce on Aug. 12, 2008).

For the implementation of simulation step 106, a model of the optical refractive indexes at each adsorption and desorption step (i.e. for each relative pressure $P_{rel}$ of the adsorbable gaseous substance in the chamber) is also required. Therefore, a dispersion law is used representing the optical index, whose parameters are adjusted at each step; the variations in the values of the real and imaginary parts of the optical index can, for example, be modelled by the laws of Cauchy, which apply particularly well to dielectric materials, for which the porosity is to be characterised: these are the functions of the wavelength $\lambda$ consisting in expressing the optical material indexes in the following manner:

$$\tilde{n}(\lambda) = \sum_{i \geq 1} \frac{a_i}{\lambda^{2(i-1)}}.$$

Most of the time, only the first two or three terms of the following sum are used: $a_1$, $a_2$ and $a_3$.

The method according to the invention also comprises a step 108 for minimising the difference between the experimental response 105 and the theoretical response 107. This minimisation is made possible by adjusting (step 109) the real and imaginary parts of the optical index so as to make the difference between the experimental response 105 and the theoretical response 107 less than or equal to a given threshold. One example of minimisation method 108 is the library-based methodology. This method enables the inverse problem to be resolved (if the direct problem is defined as the calculation of a scatterometric signature from a set of parameters, the inverse problems therefore consists in finding the set of parameters from the scatterometric signature measurement). This method consists in building a database of scatterometric signatures. Each signature originates from the simulation (therefore, for example, is calculated using an RCWA method). The method thus aims at comparing the signature acquired experimentally to all of the signatures in the database. This is a global minimisation method. Other examples of global optimisation methods can be cited, and can be used in the method according to the invention, such as neural networks or evolutionary (or genetic) algorithms. The simplex method or the Levenberg-Marquart method, which are local optimisation techniques, can also be used.

Once the optimisation has been performed through minimisation step 108, a set of coefficients $a_1$, $a_2$ and $a_3$ is obtained for each relative pressure $P_{rel}$ (when using a Cauchy law), representing the evolution of the real and imaginary parts of the optical index at the relative pressure considered. At each wavelength $\lambda$ of the spectral range used for the scatterometry measurement, an effective optical index value $n(\lambda, P_{rel})$ is i thus obtained (in this case the real part of the index) for the material constituting the pattern 2 (with a certain quantity of adsorbable gaseous substance condensed in the pores) for a given relative pressure $P_{rel}$.

As an example, FIG. 5 represents the evolution, during adsorption (curve 112) and desorption (curve 113), of an effective refractive index $n(\lambda=633 \text{ nm}, P_{rel})$ according to the relative pressure at a wavelength of 633 nm, determined by the method according to the invention. Moreover, an increasing evolution in the index is observed when the relative pressure increases, with the index increasing at a lesser rate when the relative pressure reaches a value equal to 0.2, all of the open pores of the patterns being filled when the relative pressure is equal to 1 (saturation vapour pressure of the adsorbable gaseous substance).

The method according to the invention can also comprise a step 110 for determining the quantity of adsorbable gaseous substance condensed in the pores. In order to achieve this, the index of the porous material with the condensed adsorbable gaseous substance at a given wavelength is used to determine the quantity of adsorbable gaseous substance that has condensed in the pores of the material according to the pressure of the adsorbable gaseous substance within the chamber using a law of effective medium approximation (EMA):

$$V_s(P_{rel}) = \frac{\frac{n^2(P_{rel}) - 1}{n^2(P_{rel}) + 2} - \frac{n_{vide}^2 - 1}{n_{vide}^2 + 2}}{\frac{n_s^2 - 1}{n_s^2 + 2}}$$

$$P_{rel} = P/P_s$$

where:

$V_s(P_{rel})$: the volume fraction of the adsorbable gaseous substance condensed in the pores;

P: the pressure within the chamber;

$P_s$: the saturation vapour pressure of the adsorbable gaseous substance;

$n(P_{rel})$: the effective index of the material constituting the grating (porous+condensed adsorbable gaseous substance) at the relative pressure $P_{rel}$ and at a given wavelength (i.e. $n(\lambda, P_{rel})$ for $\lambda$ given);

$n_{vide}$: the effective index of the material constituting the grating in a vacuum (possibly used during the first measurement in a vacuum for determining the dimensions of the patterns) at the same given wavelength $\lambda$;

$n_s$: the index of the adsorbable gaseous substance at the same given wavelength $\lambda$.

Figure 6:
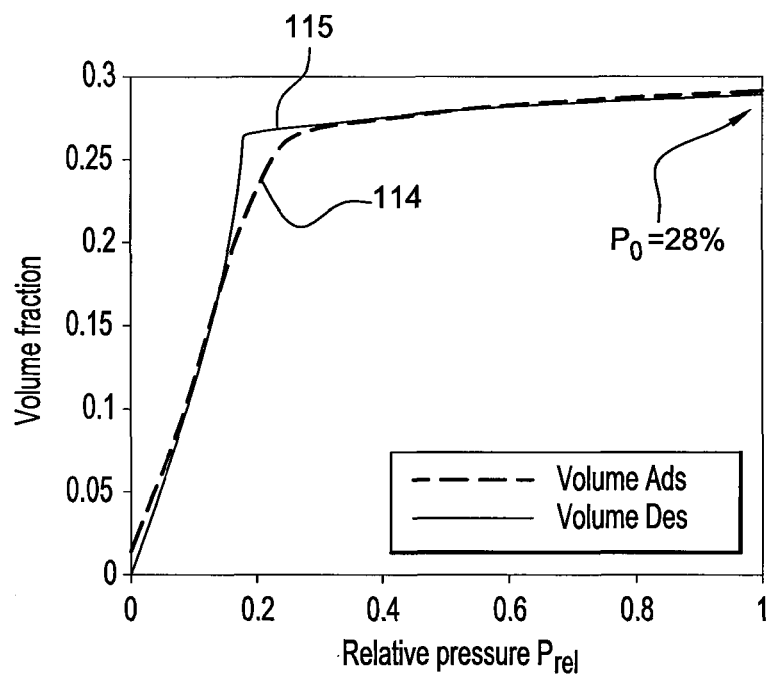
FIG. 6 represents an example of evolution, during adsorption and desorption, of the volume fraction of the adsorbable gaseous substance determined by the method according to the invention according to the relative pressure at a given wavelength.

FIG. 6 represents an example of evolution, during adsorption (curve 114) and desorption (115), of the volume fraction of the adsorbable gaseous substance determined by the method according to the invention according to the relative pressure. This volume fraction is determined using the evolution of the index represented in FIG. 5 and an EMA law as described above.

Once the saturation vapour pressure for the adsorbable gaseous substance ($P_{rel}=1$) has been reached, all of the open pores are full. Therefore, the value of the volume fraction of the condensed adsorbable gaseous substance at the saturation vapour pressure $V_s(P_{rel}=1)$ corresponds to the rate of porosity of the material (i.e. the percentage of pores in the material) creating the patterns; in this particular case, in the example in FIG. 6, the rate of porosity is equal to 28%.

The size distribution of the pores can also be calculated using Kelvin's law, which gives the radius of a cylindrical pore according to the relative pressure:

$$r = r_k + t$$

$$r_k = \frac{-2\gamma V_L \cos\theta}{RT\ln(P/P_S)}$$

where:

$r=r_k+t$ represents the radius of the pore;

t represents the thickness of the monolayer adsorbed on the walls of the pore;

$V_L$ represents the molar volume of the adsorbable gaseous substance;

$\gamma$ represents the surface stress of the adsorbable gaseous substance;

R represents the pure gas constant;

T represents the temperature;

$\theta$ represents the contact angle of the adsorbable gaseous substance on the porous material (zero for some adsorbable gaseous substances).

Figure 7:
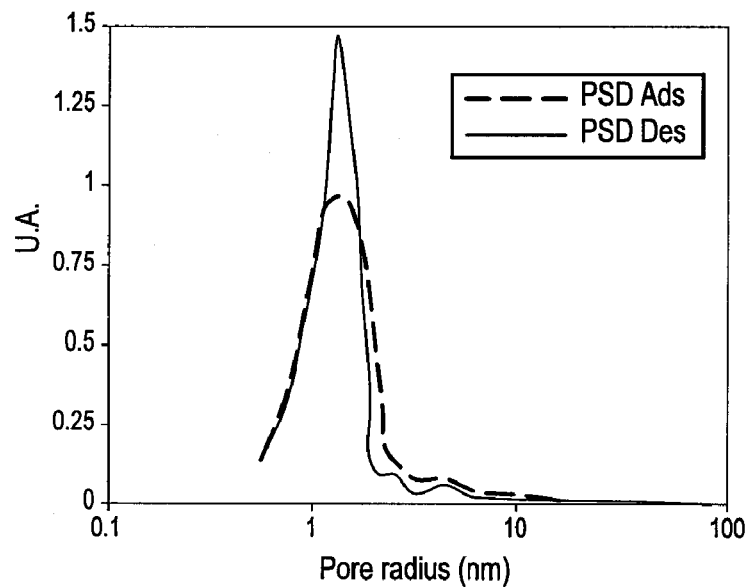
FIG. 7 represents an example of size distribution of the pores within the patterns of a structure analysed by the method according to the invention.

The adsorbable gaseous substance condenses in the pores by capillarity. Kelvin's law predicts at what pressure the adsorbable gaseous substance will condense in the pores of a given radius. In other words, the adsorbable gaseous substance, at a given pressure, can only condense by capillarity in the pores with a determined radius. This also explains why the pores with small radii are filled at a lower pressure, the pores with bigger radii then being filled at higher pressures. Therefore, via Kelvin's law and the law of effective medium approximation (EMA), the quantity of adsorbable gaseous substance condensed in the pores with the same radii (corresponding to a given pressure) can be determined. In this manner, the size distribution of the pores can be obtained; FIG. 7 represents an example of the radius distribution (expressed in nm) of the pores of the structure analysed by the method according to the invention. This distribution substantially has a Gaussian shape, centred around a radius approximately equal to 1.5 nm.

Figure 8:
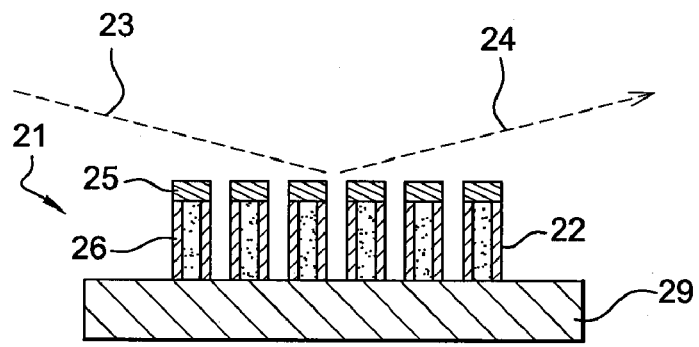
FIGS. 8 and 9 illustrate a structure to be characterised according to a second embodiment of the invention.
Figure 9:
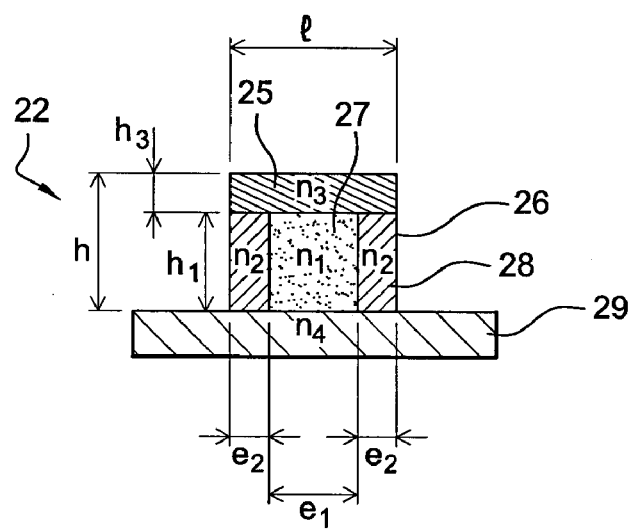

FIGS. 8 and 9 illustrate a structure 21 to be characterised according to a second embodiment of the method according to the invention, used in this example for measuring the diffusion speed of the adsorbable gaseous substance through a porous material.

In a manner identical to the first embodiment, structure 21 is lit by a specular light wave 23 at a given wavelength, emitted by a light source that is not represented; the reflected light 24 forms the experimental optical response of structure 21 being analysed. It is understood that measurements can be made using different wavelengths for the incident wave.

With the configuration of device 6 as represented in FIG. 1, an adsorbable gaseous substance can be injected into chamber 5 via supply means 9 and control valve 10, and the pressure can be varied within chamber 5 by pump 7 and control valve 8.

Structure 21 comprises a plurality of identical or substantially identical patterns 22 that are positioned periodically. These patterns 22 are preferably parallel lines spaced apart and formed on a substrate 29.

Each pattern 22 comprises a non-porous upper layer 25 positioned on the surface of a porous layer 26 being studied. The thickness of the upper layer 25 is preferably produced so as to be transparent to the wavelengths used for the scatterometry measurement so that the porous material underneath the layer can be probed (for example in the event of a stack with a hard metallic mask layer, the thickness of the metal must be thin enough: typically less than 25 nm for TiN).

During the optical measurement, in the adsorption step, the adsorbable gaseous substance condenses in the open pores on the sidewalls of the porous layer 26. If the pattern 22 is large enough, the condensation only initially takes place on the sidewalls of the pattern, then the adsorbable gaseous substance spreads from the sidewalls to the centre of the pattern 22, the speed of which varying according to the properties of the porous material.

One example of a scatterometric model that can be used for implementing the method according to the invention is provided in FIG. 9. Pattern 22 is modelled with several different index areas: one index $n_1$ for the central part 27 made out of empty porous material, one index $n_2$ on the sidewalls 28 representing the porous material filled with adsorbable gaseous substance, one index $n_3$ for the non-porous layer 25 at the surface and one index $n_4$ for the substrate 29. Thus, when the adsorbable gaseous substance is diffused, the thickness $e_2$ (thickness of the sidewalls 28) of the area filled with adsorbable gaseous substance will progressively increase to thickness $e_1$ of the central part 27, which will thus decrease. The heights of the surface and porous layers are $h_3$ and $h_1$ respectively.

Figure 10:
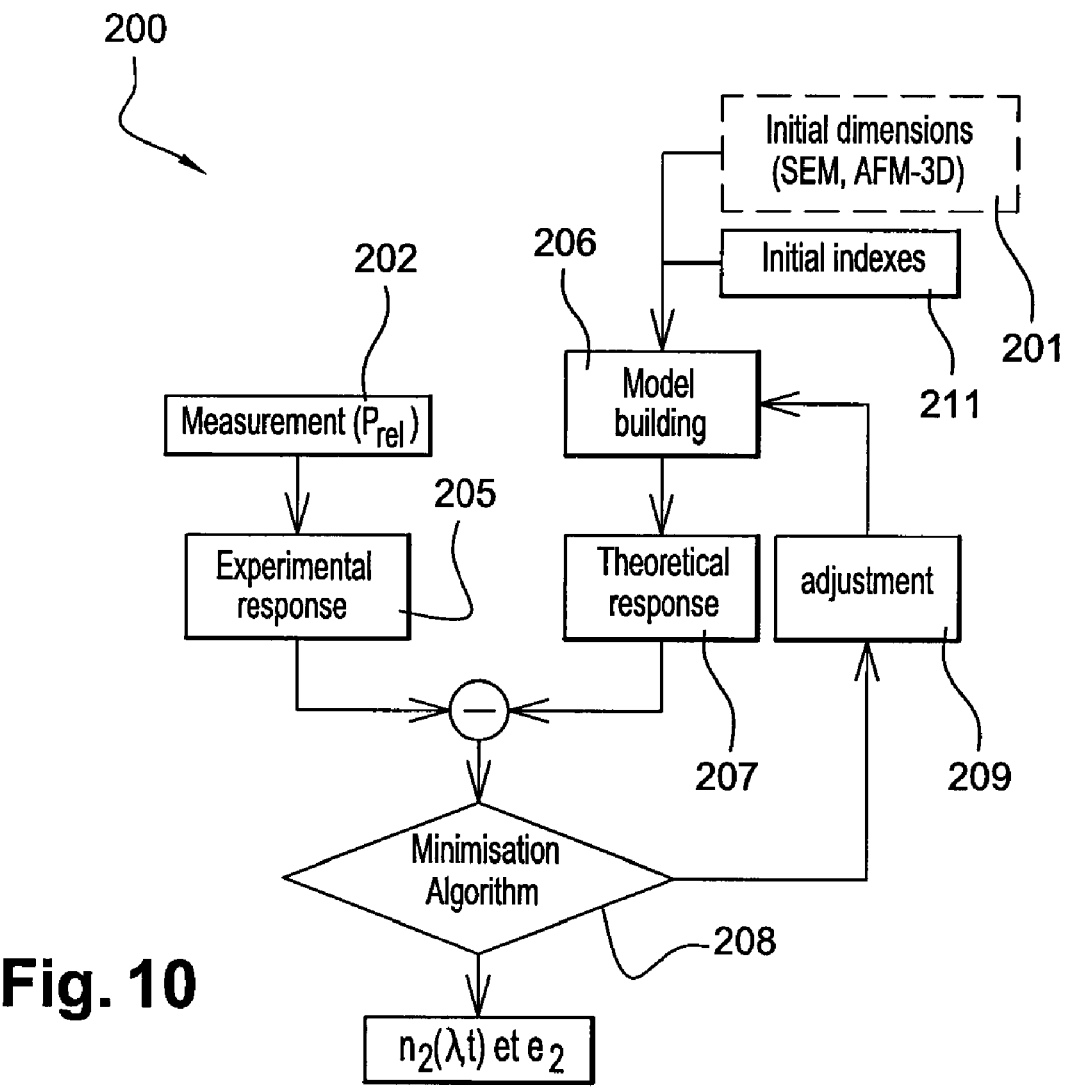
FIG. 10 illustrates a second embodiment of the method according to the invention.

The steps of the second embodiment of method 200 according to the invention, applicable to the structure in FIG. 8 are illustrated with reference to FIG. 10.

The first step 201 of method 200 according to the invention consists in determining at least one part of the dimensions (typically the total height h, heights $h_1$ and $h_3$ and width l) of patterns 22. This determination can, for example, be obtained by a measurement taken by scanning electron microscopy (SEM) or by atomic force microscopy in three dimensions (AFM-3D). A first scatterometric acquisition can also be made using the experimental optical response of diffraction structure 21 placed in chamber 5 in a residual vacuum.

A sequence for the adsorption of the adsorbable gaseous substance is then performed on structure 21 at a relative pressure $P_{rel}$ of the adsorbable gaseous substance in chamber 5, high enough to enable, by letting the adsorbable gaseous substance be diffused, all of the open pores of patterns 22 to be filled. Several scatterometric optical acquisitions 202 are performed on the porous grating so as to monitor in time the diffusion of the adsorbable gaseous substance in the porous layers 26. Unlike in the first embodiment of the method, in this example the evolution of the optical signatures of structure 21 are monitored according to the time of progression of the line of adsorbable gaseous substance through the porous material and not according to the relative pressure within the chamber.

For each porosimetric scatterometry measurement 202, the effective index $n_2$ of the porous sidewalls 26 changes according to the quantity of adsorbable gaseous substance condensed in the pores, and the geometric parameter formed by the thickness $e_2$ increases.

The method 200 according to the invention also comprises, for each time of measurement, a step 207 for determining the theoretical optical response of structure 21 using a simulation method 206. Modelling of the patterns to obtain the theoretical signature can, for example, be obtained by a rigorous coupled-wave analysis method (RCWA).

In order to implement the simulation step 26, modelling of the optical index $n_2$ of the porous sidewalls 26 at each measurement step (i.e. for each time of measurement) is also required. Therefore, a law of dispersion is used (such as the Law of Cauchy), representing the optical index whose parameters are adjusted at each step.

The method 200 according to the invention also comprises a step 208 for minimising the difference between the experimental response 205 and the theoretical response 207. This minimisation (for example using the library-based methodology) is made possible by adjusting (step 209) the real and imaginary parts of the optical index $n_2$ in addition to the thickness $e_2$, so as to make the difference between the experimental response 205 and the theoretical response 207 less than or equal to a given threshold. It should be noted that, unlike with the method according to the first embodiment, in which the dimensions were entirely determined during the first step, in this example a geometric parameter is left blank (in this case thickness $e_2$), and will be adjusted.

With the method 200 according to the invention, thickness $e_2$ is estimated according to time and the diffusion coefficient of the adsorbable gaseous substance in the porous material can thus be determined.

Figure 11:
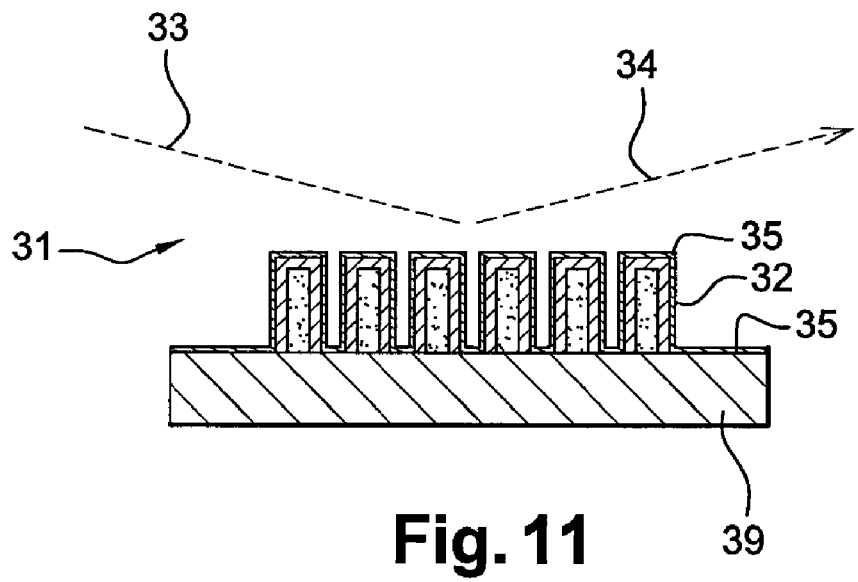
FIGS. 11 and 12 illustrate a structure to be characterised according to a third embodiment of the invention.
Figure 12:
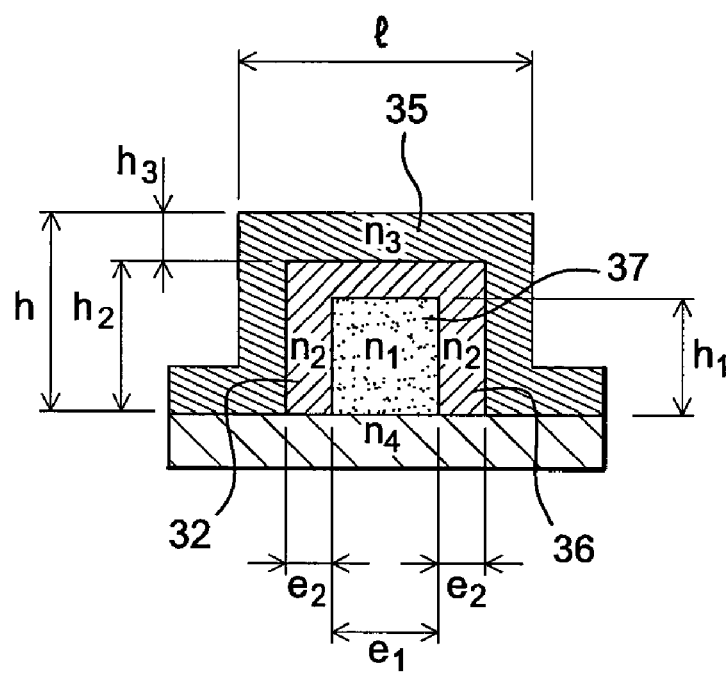

FIGS. 11 and 12 illustrate a structure 31 to be characterised according to a third embodiment of the method according to the invention, used in this example for measuring the permeability of the adsorbable gaseous substance through a material.

In a manner identical to the first embodiment, structure 31 is lit by a specular light wave 33 at a given wavelength, emitted by a light source that is not represented; the reflected light 34 forms the experimental optical response of structure 31 being analysed. It is understood that measurements can be made using different wavelengths for the incident wave.

With the configuration of device 6 as represented in FIG. 1, an adsorbable gaseous substance can be injected into chamber 5 via supply means 9 and control valve 10, and the pressure can be varied within chamber 5 by pump 7 and control valve 8.

Structure 31 comprises a plurality of identical or substantially identical patterns 32 that are positioned periodically. These patterns 32 are preferably parallel lines spaced apart and formed on a substrate 39.

A layer 35, made out of the material being studied and forming a permeable membrane, is positioned on the patterns 32 manufactured using a porous material capable of adsorbing an adsorbable gaseous substance. The layer 35 being studied is preferably transparent to the wavelengths used for the scatterometric measurement so that the porous material of patterns 32 underneath the layer 35 can be probed. During the optical measurement, in the adsorption step, the adsorbable gaseous substance penetrates at a varying rate through the membrane 35 and condenses in the open pores on the sidewalls of the porous patterns 32, which act as receptacles for the adsorbable gaseous substance. According to the properties of the membrane (more or less permeable), the condensation only initially takes place on the sidewalls 36 of the pattern 32, then the adsorbable gaseous substance spreads from the sidewalls 36 to the centre 37 of the pattern, the speed of which varying.

One example of a scatterometric model that can be used for implementing the method according to the invention is provided in FIG. 12. Pattern 32 and membrane 35 are modelled with several different index areas: one index $n_1$ for the centre 37 of the pattern 32 made out of porous material empty of adsorbable gaseous substance, one index $n_2$ on the sidewalls 36 of the pattern 32 representing the porous material filled with adsorbable gaseous substance, one index $n_3$ for the membrane 35 and one index $n_4$ for the substrate 39. The heights of the membrane 35 and the porous layer 32 are $h_3$ and $h_2$ respectively. Thus, during permeation, thickness $e_2$ of area 36 filled with the adsorbable gaseous substance will progressively increase, whereas thickness $e_1$ and height $h_1$ of the central area 37 will decrease.

The method according to this third embodiment is similar to the method 200 described with reference to FIG. 10. The difference resides in the fact that it is not the porous material that is being characterised but the permeability of the membrane located on top of the porous material, the latter acting as a storage area for the adsorbable gaseous substance. With this method according to this third embodiment, thickness $e_2$ and height $h_1$ are estimated according to time and the permeability of the membrane 35 to the adsorbable gaseous substance can thus be determined.

Figure 13:
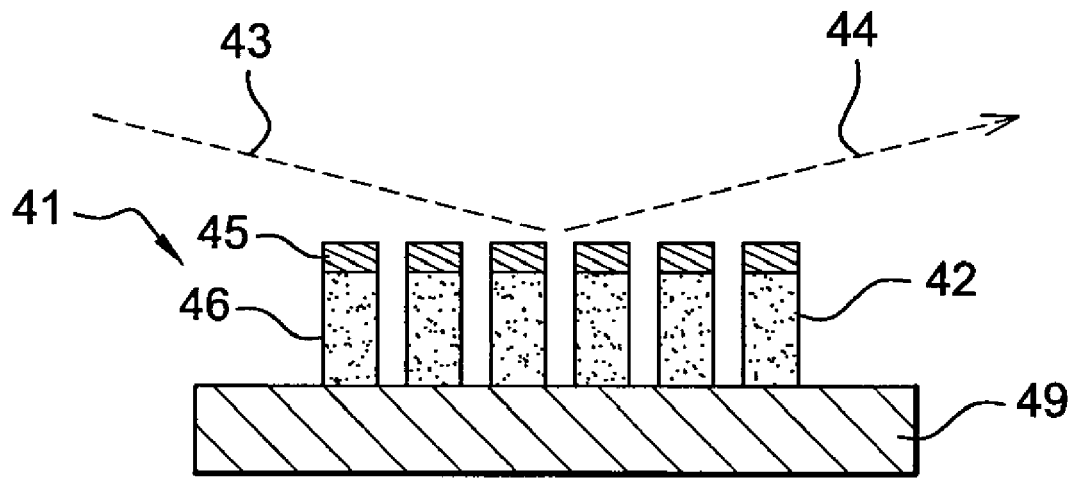
FIGS. 13 and 14 illustrate a structure to be characterised according to a fourth embodiment of the invention.
Figure 14:
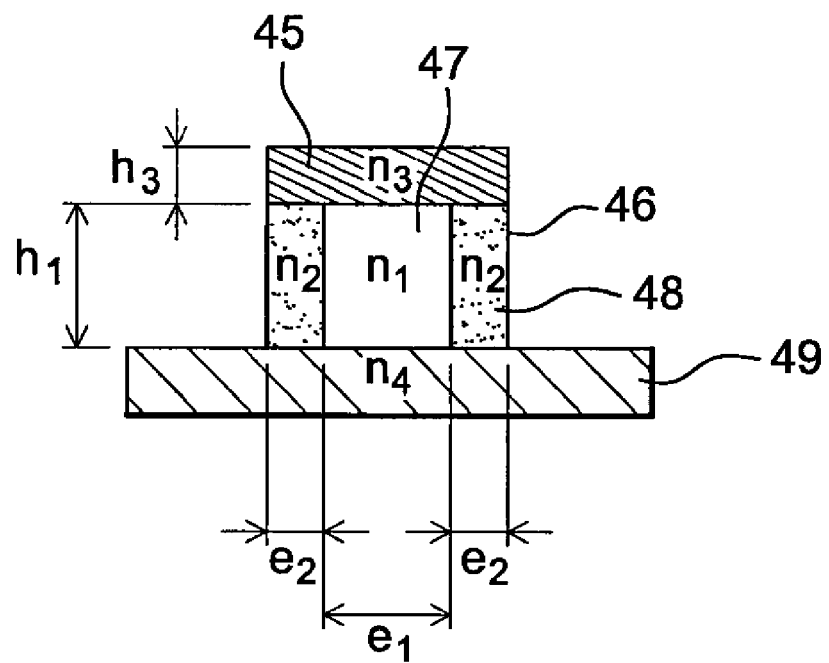

FIGS. 13 and 14 illustrate a structure 41 to be characterised according to a fourth embodiment of the method according to the invention, used in this example for measuring the damage caused to a porous material when it is integrated into a microelectronic circuit (in particular during etching, stripping or cleaning processes).

In a manner identical to the first embodiment, structure 41 is lit by a specular light wave 43 at a given wavelength, emitted by a light source that is not represented; the reflected light 44 forms the experimental optical response of structure 41 being analysed. It is understood that measurements can be made using different wavelengths for the incident wave.

With the configuration of device 6 as represented in FIG. 1, an adsorbable gaseous substance can be injected into chamber 5 via supply means 9 and control valve 10, and the pressure can be varied within chamber 5 by pump 7 and control valve 8.

Structure 41 comprises a plurality of identical or substantially identical patterns 42 that are positioned periodically. These patterns 42 are preferably parallel lines spaced apart and formed on a substrate 49.

Each pattern 42 comprises a non-porous upper layer 45 positioned on the surface of a porous layer 46 being studied. The thickness of the upper layer 45 is preferably produced so as to be transparent to the wavelengths used for the scatterometric measurement so that the porous material of patterns underneath the layer can be probed. The porous material of the porous layer 46 is then subjected to the processes dedicated to its integration (typically lithography, etching, stripping and cleaning processes, etc.). During these steps, a modified (damaged) layer of the porous material can be formed on the parts of the patterns that are not protected during the aforementioned steps (for example on the sidewalls 48 of patterns 42, which are not masked by another material). The wettability properties of the damaged material are thus different to those of the initial porous material.

One example of a scatterometric model that can be used for implementing the method according to the invention is provided in FIG. 14. Pattern 42 is modelled with several different index areas: one index $n_1$ for the central area made out of empty porous material, one index $n_2$ on the sidewalls 48 of pattern 42 representing the damaged porous material, one index $n_3$ for the non-porous layer 45 at the surface and one index $n_4$ for the substrate 49.

During the optical measurement, in the adsorption step, the vapour of a polar solvent such as water will be used as the adsorbable gaseous substance and will be condensed on the damaged sidewalls 48 only (hydrophilic area) of patterns 42 and not in the central area 47 that remains unchanged (hydrophobic area). In order to improve the precision of the results, the width of the lines forming patterns 42 can advantageously be reduced so that the changed area 48 of the material is significant in size when compared to the unchanged area 47.

Thus, during the adsorption step, only the damaged area 48 is filled with polar solvent and the geometric parameter $e_2$ (thickness of the damaged area 48) provides the size of the damaged area. The heights of the surface layer 45 and porous layer 46 are $h_3$ and $h_1$ respectively.

The method according to this fourth embodiment of the invention is fairly similar to the method according to the first embodiment illustrated in FIG. 4.

Thus, the first step of the method according to the fourth embodiment consists in determining at least one part of the dimensions of patterns 32 (typically the height and width h and l of the patterns in addition to the heights of the surface layer 45 and porous layer 46 $h_3$ and $h_1$).

A sequence for the adsorption (and possibly desorption) of the polar solvent is performed on structure 31 whereas scatterometric optical acquisition is performed in parallel on the porous grating for each pressure of the polar solvent within chamber 5. An experimental optical response is thus obtained according to the wavelength for each relative pressure $P_{rel}$ of the polar solvent in chamber 5.

The method according to this fourth embodiment also comprises, for each relative pressure $P_{rel}$, a step for determining the theoretical optical response of structure 31 using a simulation method. Modelling of the patterns to obtain the theoretical signature can, for example be obtained by a rigorous coupled-wave analysis method (RCWA).

In order to implement the simulation step, modelling of the optical index $n_2$ of the sidewalls 36 at each measurement step (i.e. for each relative pressure) is also required. Therefore, a law of dispersion is used (such as the Law of Cauchy), representing the optical index whose parameters are adjusted at each step.

The method according to the fourth embodiment of the invention additionally comprises a step for minimising the difference between the experimental response and the theoretical response. This minimisation is made possible by adjusting the real and imaginary parts of the optical index $n_2$ in addition to the thickness $e_2$ so as to make the difference between the experimental response and the theoretical response less than or equal to a given threshold. It should be noted that, unlike with the method according to the first embodiment, in which the dimensions were entirely determined during the first step, in this example a geometric parameter is left blank (in this case thickness $e_2$), and will be adjusted. Thus, the method according to this fourth embodiment practiced on structure 41 enables the thickness $e_2$ of the damaged porous material to be determined by modelling.

In a general manner, it is thus noted that the principle of the invention rests on performing porosimetric measurements directly on the periodic patterns by using scatterometry to analyse their optical signature and on adapting the scatterometric analysis to the problematic of porosity, not by adjusting the dimensions of the patterns but by adjusting their index at each step of measurement (the different measurements capable of being performed by varying the relative pressure of the adsorbable gaseous substance used or according to the time of diffusion of the adsorbable gaseous substance within the pattern).

Of course, the invention is not limited to the aforementioned modes of embodiment.

In particular, even if the invention was described in more detail in the event of an approach using ellipsometric scatterometry (i.e. using the change in polarisation of light) or spectroscopic scatterometry (i.e. in which the wavelength of the incident light is varied), the invention can be applied to any type of scatterometric method such as variable angle ellipsometry (also referred to as goniometry or θ-2θ) or reflectometry (spectroscopic or goniometric).

The invention claimed is:

1. A method for the optical characterisation of repeat units repeated in a regular manner so as to form a diffraction structure, each repeat unit comprising at least one geometric pattern, each of said patterns being produced, at least in part, using a porous material, said method comprising:
    determining the geometric parameters of said patterns;
    performing a scatterometric acquisition using an optical measurement system of the experimental optical response of said diffraction structure placed in a chamber at a given pressure, a presence of an adsorbable gaseous substance in said chamber causing condensation of said adsorbable gaseous substance in at least one part of open pores of the patterns of the structure; and
    determining a theoretical optical response of said diffraction structure from the determined geometric parameters and by adjusting an optical index of the material of an area of each of said patterns, in which the adsorbable gaseous substance has condensed, so as to make a difference between said experimental response and said theoretical response less than or equal to a given threshold.

2. The method according to claim 1, wherein the size of said diffraction structure is larger than the size of an optical spot used for the scatterometric measurement.

3. The method according to claim 1, wherein said diffraction structure comprises at least ten patterns.

4. The method according to claim 1, wherein each pattern is a line made out of dielectric material capable of insulating two metallic lines.

5. The method according to claim 1, wherein the scatterometric acquisition is performed by ellipsometry.

6. The method according to claim 1, wherein determining the geometric parameters of said patterns comprises performing a scatterometric acquisition of the experimental optical response of said diffraction structure placed in the chamber in a vacuum and determining the theoretic optical response of said diffraction structure from the optical indexes of the patterns in a vacuum and by adjusting the dimensions of said patterns so as to make the difference between said experimental response and said theoretical response less than or equal to a given threshold.

7. The method according to claim 1, wherein determining the geometric parameters of said patterns comprises measuring by scanning electron microscopy and/or by atomic force microscopy in three dimensions.

8. The method according to claim 1, comprising performing a plurality scatterometric acquisitions at different given pressures, each acquisition being followed by determining the theoretical optical response of the diffraction structure by adjusting the optical index.

9. The method according to claim 8, comprising determining said optical index, adjusted according to pressure over the entire range of wavelengths used for the scatterometric acquisition.

10. The method according to claim 8, wherein said plurality of scatterometric acquisitions at different given pressures is performed according to an increasing variation in pressure corresponding to the progressive adsorption of said adsorbable gaseous substance in the open pores of said patterns and/or according to a decreasing variation in pressure corresponding to the progressive desorption of said adsorbable gaseous substance in the open pores of said patterns.

11. The method according to claim 10, wherein the pressure varies from a residual vacuum pressure to the saturation vapour pressure of said adsorbable gaseous substance and/or from the saturation vapour pressure of said adsorbable gaseous substance to a residual vacuum pressure.

12. The method according to claim 1, wherein the optical index of the adjusted material at a given pressure is used to determine the quantity of adsorbable gaseous substance that has condensed in the open pores.

13. The method according to claim 12, wherein determining the quantity of adsorbable gaseous substance condensed is performed by determining the volume fraction of the adsorbable gaseous substance condensed in the open pores via a law of effective medium approximation (EMA).

14. The method according to claim 13, comprising determining the size distribution of the open pores.

15. The method according to claim 12, wherein the value of the rate of apparent porosity of said porous material forming, at least in part, said patterns, is obtained by adjusting the optical index to the saturation vapour pressure of said adsorbable gaseous substance.

16. The method according to claim 1, wherein each of said patterns comprises a first upper layer made out of a non-porous material positioned on the surface of a second layer comprising at least one part made out of a material not capable of adsorbing the adsorbable gaseous substance used when the latter is maintained under pressure in contact with the material, and at least one part, such as one of its sidewalls, made out of a porous material, the difference between the experimental response at a given pressure and the theoretical response being made less than or equal to a given threshold by adjusting:

the optical index of the material of the area of said porous part in which the adsorbable gaseous substance has condensed; and a geometric parameter representing the size of the area of said porous part in which the adsorbable gaseous substance has condensed;

said method comprising a plurality of scatterometric acquisitions at different given pressures, each acquisition being followed by determining the theoretical optical response of the diffraction structure by adjusting said optical index and said geometric parameter.

17. The method according to claim 16, wherein said adsorbable gaseous substance is a polar solvent such as water.

18. The method according to claim 16, wherein the material of the non-porous layer in addition to its thickness are chosen so that said non-porous layer is transparent to the wavelengths used for the scatterometric acquisitions.

19. The method according to claim 1, wherein each of said patterns comprises a first upper layer made out of a non-porous material positioned on the surface of a second layer made out of a porous material, the difference between the experimental response at a given pressure and the theoretical response being made less than or equal to a given threshold by adjusting:

the optical index of the material of the area of said second layer in which the adsorbable gaseous substance has condensed; and a geometric parameter representing the size of the area of said second porous layer in which the adsorbable gaseous substance has condensed;

said method comprising a plurality of scatterometric acquisitions according to the time of diffusion of said adsorbable gaseous substance within said second layer from the sidewalls of the latter, each acquisition being followed by determining the theoretical optical response of the diffraction structure by adjusting said optical index and said geometric parameter.

20. The method according to claim 1, wherein an upper layer made out of a permeable material to be characterised is positioned on the upper surface of the patterns made out of a porous material, the difference between the experimental response at a given pressure and the theoretical response being made less than or equal to a given threshold by adjusting:

the optical index of the material of the area of said porous patterns in which the adsorbable gaseous substance has condensed; and a geometric parameter representing the size of the area of said porous patterns in which the adsorbable gaseous substance has condensed;

said method comprising a plurality of scatterometric acquisitions according to the time of diffusion of said adsorbable gaseous substance within said patterns from the sidewalls of the latter, each acquisition being followed by determining the theoretical optical response of the diffraction structure by adjusting said optical index and said geometric parameter.

21. The method according to claim 1, wherein determining the theoretical optical response of said diffraction structure is performed by a rigorous coupled-wave analysis method (RCWA).

22. The method according to claim 1, wherein the optical measurement system includes an ellipsometry device or a reflectometry device.

* * * * *